United States Patent
Svanerudh (10) Patent No.: US 11,883,138 B2
(45) Date of Patent: *Jan. 30, 2024

(54) CARDIAC CYCLE-BASED DIAGNOSTIC SYSTEMS AND METHODS

(71) Applicant: ST. JUDE MEDICAL COORDINATION CENTER BVBA, Zaventem (BE)

(72) Inventor: Johan Svanerudh, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 41 days.

This patent is subject to a terminal disclaimer.

(21) Appl. No.: 17/733,010

(22) Filed: Apr. 29, 2022

(65) Prior Publication Data
US 2022/0257127 A1    Aug. 18, 2022

Related U.S. Application Data

(63) Continuation of application No. 14/837,291, filed on Aug. 27, 2015, now Pat. No. 11,350,832.
(Continued)

(51) Int. Cl.
*A61B 5/0215* (2006.01)
*A61B 5/00* (2006.01)
(Continued)

(52) U.S. Cl.
CPC ........ *A61B 5/02154* (2013.01); *A61B 5/0035* (2013.01); *A61B 5/0066* (2013.01);
(Continued)

(58) Field of Classification Search
None
See application file for complete search history.

(56) References Cited

U.S. PATENT DOCUMENTS

| 5,321,501 A | 6/1994 | Swanson et al. |
| 5,459,570 A | 10/1995 | Swanson et al. |

(Continued)

FOREIGN PATENT DOCUMENTS

| EP | 1 260 175 A2 | 11/2002 |
| JP | 2004-538035 A | 12/2004 |

(Continued)

OTHER PUBLICATIONS

Allen et al., "Multicenter Core Laboratory Comparison of the Instantaneous Wave-Free Ratio and Resting Pd/Pa With Fractional Flow Reserve the RESOLVE Study", Journal of the American College of Cardiology, vol. 63, No. 13, Apr. 8, 2017, pp. 1253-1261.
(Continued)

*Primary Examiner* — Yi-Shan Yang
(74) *Attorney, Agent, or Firm* — Foley & Lardner LLP (57) ABSTRACT

A method of determining one or more diagnostic metrics to assess a blood vessel using intravascular data includes: sampling a sensor of an intravascular data collection probe disposed in the blood vessel during a pullback of the intravascular data collection probe through the blood vessel to obtain sampled distal pressure (Pd) values; receiving, at an intravascular data processing system, the sampled distal pressure (Pd) values and proximal pressure (Pa) values; determining sets of Pd/Pa ratios, each set including Pd/Pa ratios that are determined through an entirety of one heart cycle; determining minimum Pd/Pa ratios, each of which is a minimum within one of the sets of Pd/Pa ratios over the entirety of the corresponding heart cycle; and controlling a display system to generate a plot of a moving average of the minimum Pd/Pa ratios over time during the pullback.

14 Claims, 8 Drawing Sheets

Related U.S. Application Data (60) Provisional application No. 62/042,448, filed on Aug. 27, 2014.

(51) Int. Cl.
*A61B 5/026* (2006.01)
*A61B 5/02* (2006.01)
*A61B 8/04* (2006.01)
*A61B 6/00* (2006.01)
*A61B 90/00* (2016.01)

(52) U.S. Cl.
CPC ............ *A61B 5/0084* (2013.01); *A61B 5/026* (2013.01); *A61B 5/0215* (2013.01); *A61B 5/7203* (2013.01); *A61B 5/7278* (2013.01); *A61B 5/742* (2013.01); *A61B 5/02007* (2013.01); *A61B 6/504* (2013.01); *A61B 8/04* (2013.01); *A61B 2090/3782* (2016.02); *A61B 2576/00* (2013.01)

(56) References Cited

U.S. PATENT DOCUMENTS

| | | |
|---|---|---|
| 5,465,147 A | 11/1995 | Swanson |
| 5,509,093 A | 4/1996 | Miller et al. |
| 5,619,368 A | 4/1997 | Swanson |
| 5,748,598 A | 5/1998 | Swanson et al. |
| 5,784,352 A | 7/1998 | Swanson et al. |
| 5,965,355 A | 10/1999 | Monis et al. |
| 6,111,645 A | 8/2000 | Tearney et al. |
| 6,134,003 A | 10/2000 | Tearney et al. |
| 6,160,826 A | 12/2000 | Swanson et al. |
| 6,191,862 B1 | 2/2001 | Swanson et al. |
| 6,282,011 B1 | 8/2001 | Tearney et al. |
| 6,421,164 B2 | 7/2002 | Tearney et al. |
| 6,445,939 B1 | 9/2002 | Swanson et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,570,659 B2 | 5/2003 | Schmitt |
| 6,706,004 B2 | 3/2004 | Tearney et al. |
| 6,865,419 B2 | 3/2005 | Mulligan et al. |
| 6,879,851 B2 | 4/2005 | Mcnamara et al. |
| 6,891,984 B2 | 5/2005 | Petersen et al. |
| 7,208,333 B2 | 4/2007 | Flanders et al. |
| 7,231,243 B2 | 6/2007 | Tearney et al. |
| 7,241,286 B2 | 7/2007 | Atlas |
| 7,324,848 B1 * | 1/2008 | Turcott ............ A61B 5/14551 607/9 |
| 7,414,779 B2 | 8/2008 | Huber et al. |
| 7,415,049 B2 | 8/2008 | Flanders et al. |
| 7,625,366 B2 | 12/2009 | Atlas |
| 7,813,609 B2 | 10/2010 | Petersen et al. |
| 7,848,791 B2 | 12/2010 | Schmitt et al. |
| 7,916,387 B2 | 3/2011 | Schmitt |
| 7,935,060 B2 | 5/2011 | Schmitt et al. |
| 8,116,605 B2 | 2/2012 | Petersen et al. |
| 8,206,377 B2 | 6/2012 | Petroff |
| 8,298,156 B2 | 10/2012 | Manstrom et al. |
| 8,325,419 B2 | 12/2012 | Schmitt |
| 8,358,461 B2 | 1/2013 | Huber et al. |
| 8,412,312 B2 | 4/2013 | Judell et al. |
| 8,449,468 B2 | 5/2013 | Petersen et al. |
| 8,478,384 B2 | 7/2013 | Schmitt et al. |
| 8,478,387 B2 | 7/2013 | Xu |
| 8,503,844 B2 | 8/2013 | Petersen et al. |
| 8,581,643 B1 | 11/2013 | Schmitt |
| 8,582,109 B1 | 11/2013 | Schmitt |
| 8,582,619 B2 | 11/2013 | Adler |
| 8,582,934 B2 | 11/2013 | Adler et al. |
| 8,687,201 B2 | 4/2014 | Adler |
| 8,786,336 B1 | 7/2014 | Schmitt |
| 8,831,321 B1 | 9/2014 | Elbasiony |
| 8,948,228 B2 | 2/2015 | Adler |
| 8,953,911 B1 | 2/2015 | Xu et al. |
| 9,152,757 B2 | 10/2015 | Taylor |
| 10,912,463 B2 | 2/2021 | Davies et al. |
| 11,311,200 B1 | 4/2022 | Gopinath et al. |
| 2002/0072880 A1 * | 6/2002 | Svanerudh ........... A61B 5/0215 702/189 |
| 2002/0161351 A1 | 10/2002 | Samson et al. |
| 2005/0201662 A1 | 9/2005 | Petersen et al. |
| 2006/0095065 A1 | 5/2006 | Tanimura et al. |
| 2009/0174931 A1 | 7/2009 | Huber et al. |
| 2009/0306520 A1 | 12/2009 | Schmitt et al. |
| 2010/0076320 A1 | 3/2010 | Petersen et al. |
| 2011/0071404 A1 | 3/2011 | Schmitt et al. |
| 2011/0101207 A1 | 5/2011 | Schmitt |
| 2011/0157686 A1 | 6/2011 | Huber et al. |
| 2011/0190586 A1 | 8/2011 | Kemp |
| 2011/0228280 A1 | 9/2011 | Schmitt et al. |
| 2012/0238869 A1 | 9/2012 | Schmitt et al. |
| 2012/0250028 A1 | 10/2012 | Schmitt et al. |
| 2012/0310081 A1 | 12/2012 | Adler et al. |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0046190 A1 | 2/2013 | Davies |
| 2013/0051728 A1 | 2/2013 | Petroff et al. |
| 2013/0072805 A1 | 3/2013 | Schmitt et al. |
| 2013/0310698 A1 | 11/2013 | Judell et al. |
| 2014/0018669 A1 | 1/2014 | Xu |
| 2014/0024931 A1 | 1/2014 | Winston et al. |
| 2014/0094697 A1 | 4/2014 | Petroff et al. |
| 2014/0114182 A1 | 4/2014 | Petersen et al. |
| 2014/0135633 A1 | 5/2014 | Anderson et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0181716 A1 | 6/2014 | Merritt et al. |
| 2014/0187929 A1 | 7/2014 | Schmitt et al. |
| 2014/0218742 A1 | 8/2014 | Adler |
| 2014/0249407 A1 | 9/2014 | Adler et al. |
| 2014/0268167 A1 | 9/2014 | Friedman et al. |
| 2014/0276011 A1 | 9/2014 | Schmitt et al. |
| 2014/0276137 A1 | 9/2014 | Burnett et al. |
| 2014/0309536 A1 | 10/2014 | Douk et al. |
| 2014/0379269 A1 | 12/2014 | Schmitt |
| 2015/0025398 A1 * | 1/2015 | Davies ................. A61B 5/0215 600/486 |
| 2015/0119705 A1 | 4/2015 | Tochterman et al. |
| 2015/0119707 A1 | 4/2015 | Petroff |
| 2015/0153157 A1 | 6/2015 | Schmitt et al. |
| 2015/0192405 A1 | 7/2015 | Schmitt |
| 2015/0230713 A1 | 8/2015 | Merritt et al. |
| 2015/0313478 A1 | 11/2015 | Veszelei et al. |
| 2016/0007866 A1 | 1/2016 | Tochterman et al. |
| 2016/0008084 A1 | 1/2016 | Merritt et al. |
| 2016/0073972 A1 | 3/2016 | Alpert et al. |
| 2016/0135757 A1 | 5/2016 | Anderson et al. |
| 2016/0157785 A1 | 6/2016 | Merritt et al. |

FOREIGN PATENT DOCUMENTS

| | | |
|---|---|---|
| JP | 2012-501807 A | 1/2012 |
| JP | 2014-061268 A | 4/2014 |
| JP | 2014-151010 A | 8/2014 |
| JP | 2014-519387 A | 8/2014 |
| JP | 2014-529442 A | 11/2014 |
| WO | WO-01/13779 A2 | 3/2001 |
| WO | WO-02/43584 A2 | 6/2002 |
| WO | WO-2006/041346 | 4/2006 |
| WO | WO-2012/166332 A1 | 12/2012 |
| WO | WO-2013/145638 | 10/2013 |
| WO | WO-2016/092403 | 6/2016 |

OTHER PUBLICATIONS

Canadian Office Action, Application No. 2959205, dated Jun. 17, 2021, 5 pages.

(56) References Cited

OTHER PUBLICATIONS

International Search Report and Written Opinion for International Application No. PCT/EP2015/069708 mailed from the International Searching Authority dated Dec. 17, 2015 (13 pages).
International Search Report and Written Opinion for International Application No. PCT/EP2015/069708 mailed from the International Searching Authority dated Dec. 17, 2015 (13 pages).
Japanese Office Action and English translation, Application No. 2020-079926, dated May 18, 2021, 7 pages.
Japanese Search Report, Application No. 2020-079926, dated Apr. 21, 2021, and English translation, 50 pages.
Jeremias et al., "Multicenter Core laboratory Comparison of the Instantaneous Wave-Free Ratio and Resting Pd/Pa Nith Fractional Flow Reserve The RESOLVE Study", Journal of the American College of Cardiology, 63:13, pp. 1253-1261 (Apr. 8, 2014).
Jeremias et al., "Multicenter Core Laboratory Comparison of the Instantaneous Wave-Free Ratio and Resting Pd/Pa With Fractional Flow Reserve the RESOLVE Study", Journal of the American College of Cardiology, 63:13, pp. 253-1261 (Apr. 8, 2014).
Mamas et al., "Resting Pd/Pa Measured with Intracoronary Pressure Wire Strongly Predicts Fractional Flow Reserve", Journal of Invasive Cardiology June http://jic.epubxpress.com, 22:6, Jun. 2010, pp. 260-265.
Notice of Allowance on U.S. Appl. No. 16/186,040, datedOct. 29, 2021.
Notice of Allowance, U.S. Appl. No. 16/186,040, dated Oct. 29, 2021, 16 pages.
USPTO Notice of Allowance, U.S. Appl. No. 16/186,040, dated Feb. 25, 2022, 10 pages.
USPTO Office Action, U.S. Appl. No. 14/837,291, dated Jan. 8, 2021, 23 pages.
USPTO Office Action, U.S. Appl. No. 14/837,291, dated Mar. 27, 2020, 38 pages.
USPTO Office Action, U.S. Appl. No. 14/837,291, dated Sep. 22, 2017, 29 pages.
USPTO Office Action, U.S. Appl. No. 16/186,040, dated Feb. 4, 2021, 40 pages.
USPTO Office Action, U.S. Appl. No. 16/186,040, dated Jun. 28, 2021, 15 pages.
Notice of Reasons for Rejection issued in Japanese application No. 2022-199292, dated Aug. 22, 2023 (4 pages).
Office Action issued in Canadian Application No. 2,959,205, dated Oct. 24, 2023.

* cited by examiner

CARDIAC CYCLE-BASED DIAGNOSTIC SYSTEMS AND METHODS

RELATED APPLICATIONS

This application is a continuation of U.S. application Ser. No. 14/837,291, filed on Aug. 27, 2015, now U.S. Pat. No. 11,350,832, and claims the benefit of priority under 35 U.S.C. 119(e) from U.S. Provisional Application No. 62/042,448 filed on Aug. 27, 2014, the disclosures of which are herein incorporated by reference in their entireties.

BACKGROUND

Coronary artery disease is one of the leading causes of death worldwide. The ability to better diagnose, monitor, and treat coronary artery diseases can be of life saving importance. Various techniques can be used to obtain intravascular data such as via measured parameters or signals suitable for imaging or characterizing an artery. A measurement or sensing device such as a pressure or flow sensor (or other intravascular device) can be used to collect data and measure cardiovascular and blood vessel parameters such as length, diameter, and other parameters. Other data collection modalities such as imaging modalities can also be used to help diagnose stenosis and other cardiac system phenomena.

Intravascular optical coherence tomography (OCT) is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution. This is achieved by pullback an OCT probe through an artery of interest to obtain such details. OCT images provide high-resolution visualization of coronary artery morphology and can be used alone or in combination with other information such as pressure data or other data collecting with a sensing device. Ultrasound based devices such as intravascular ultrasound or IVUS systems and probes can also be used to collect information relating to a subject's cardiovascular system such as by imaging or measuring an artery. OCT, IVUS, and pressure data relating to a subject of interest provide a substantial amount of data about a given cardiovascular system and subsystems and components thereof.

Identifying new diagnostic metrics that advance the field of cardiovascular intervention and other research while avoiding unnecessary complications and assumptions are useful to help simplify and distill the information available to a clinician or other end user of OCT, IVUS, pressure sensing, and other intravascular data collection tools and devices.

The present disclosure addresses these challenges and others.

SUMMARY

In part, the disclosure relates to computer-based methods, and systems suitable for evaluating a cardiac system using a pressure value-based ratio or other diagnostic metrics as described herein. The pressure value-based ratio can be determined using a proximal pressure identified as Pa which can include an aortic pressure and a distal pressure Pd such as a pressure value obtained at a region located downstream from a stenosis. These pressure values can be obtained by sampling two sources of pressure data. Some exemplary sources of pressure data can include a pressure sensor such as an electrical or optical pressure transducer. Suitable pressure sensors can be disposed on, in or otherwise relative to a catheter, such as for example a delivery catheter, an intravascular data collection probe, a guidewire, and other suitable devices and systems. A ratio of Pd/Pa can be determined for each sampled Pd and Pa value of one or more cardiac cycles. A minimum value of each such Pd/Pa ratio can be determined for each cardiac cycle. The set of such minimum values also referred to as MCR values can be plotted over time. The MCR values can be displayed as numerical values or used as inputs to generate other ratios or indices relating to cardiac cycle behavior.

In part, the disclosure relates to a method of tracking cardiac cycle events using intravascular data. The method can include sampling an intravascular data collection probe at a sampling rate to obtain a first plurality of pressure values from a distal region of a vessel; receiving a second plurality of pressure values, at an intravascular data processing system, obtained from a proximal region of the vessel; determining a plurality of distal pressure to proximal pressure (Pd/Pa) ratios from the first plurality of pressure values and the second plurality of pressure values; determining a minimum Pd/Pa ratio from the plurality of Pd/Pa ratios; and displaying the minimum Pd/Pa ratio (MCR).

In one embodiment, the displayed MCR is for a first heart cycle, further comprising determining a plurality of MCRs on a per heart cycle basis. In one embodiment, the method further includes displaying an angiography cine and the plurality of MCRs over time as a pressure wire is pulled back through the vessel. In one embodiment, the method further includes repeating the steps for a plurality of subsequent heart cycles to determine a plurality of MCRs and plotting the plurality of MCRs over time on a per cardiac cycle basis. In one embodiment, the sampling rate ranges from about 25 Hz to about 2 Khz. In one embodiment, the method further includes filtering a waveform generated using a plurality of Pd/Pa ratio values prior to determining one or more minimum Pd/Pa ratios on a per cardiac cycle basis. In one embodiment, the disclosure relates to a diagnostic metric correlated with a patient state of interest that is determined using measurements obtained during a resting condition without hyperemic agents. In one embodiment, the disclosure relates to a diagnostic metric correlated with a patient state of interest that is determined using measurements obtained during a resting condition with a hyperemic agent.

In one embodiment, the MCR is a stenosis diagnostic metric, and the method further comprising monitoring MCR values over a time period T and identifying changes in the MCR value as an indication of a stenosis in the vessel. In one embodiment, the method further includes filtering a waveform generated using a plurality of Pd/Pa ratio values using a filter having a time constant and setting the time constant to correspond to a fraction of a duration of a cardiac cycle. In one embodiment, the TC can range from about 1% to about 50% of a heart cycle length. In one embodiment, the first plurality of pressure values and the second plurality of pressure values are obtained during one or more cardiac cycles that includes diastole and systole. In one embodiment, the method includes displaying a user interface comprising a first panel and a second panel, the first panel comprising a per cycle plot of MCR values and the second panel comprising one or more of a FFR value, a Pd value, a Pa value, a time value, or a MCR value.

In part, the disclosure relates to a method of analyzing cardiac cycle events in response to a pressure-value based ratio. The method can include receiving a first pressure value measured at a location distal to a region of a blood vessel (Pd1); receiving a first pressure value measured at a location proximal to a region of a blood vessel (Pa1); determining a first ratio of the first pressure value and the second pressure value (R1), wherein R1 corresponds to a first time value; receiving a third pressure value measured at a location distal to a region of a blood vessel (Pd2); receiving a fourth pressure value measured at a location proximal to a region of a blood vessel (Pa2); determining a second ratio of the third pressure value and the fourth pressure value (R2), wherein R2 corresponds to a second time value; and displaying R1 or a plot thereof versus time, if R1 is greater than R2, or displaying R2 or a plot thereof versus time, if R2 is greater than R1. In one embodiment, if R1 is greater than R2, than the first time value corresponds to an occurrence of a pressure reduction in a cardiac cycle. In one embodiment, the pressure reduction is a relative maximum. In one embodiment, the pressure reduction is a maximum for a plurality of cardiac cycles. In one embodiment, the method includes displaying a user interface comprising a first panel and a second panel, the first panel comprising a per cycle plot of MCR values and the second panel comprising one or more of a FFR value, a Pd value, a Pa value, a time value, or a MCR value, wherein the MCR value is R1 or R2.

In part, the disclosure relates to an intravascular data collection system. The system can include an intravascular data collection system comprising an interface to receive data from an intravascular probe; a display system in electrical communication with the intravascular data collection system; one or more memory storage devices comprising instructions to output a user interface on the display system, the user interface comprising one or more regions for displaying a minimum cycle ratio or a plot thereof; a processor in electrical communication with the intravascular data collection system, the display system, and one or more memory storage devices, the processor programmed to sample a plurality of proximal pressure values (Pa) on a per cardiac cycle basis; sample a plurality of distal pressure values (Pd) on a per cardiac cycle basis; determine a set of Pd/Pa ratios for one or more of the sampled Pa and sampled Pd; and identify a minimum ratio value in the set. Some non-limiting examples of intravascular data collection and analysis systems or a component thereof can include a RadiAnalyzer, a RadiAnalyzer Xpress, a Quantien, a PressureWire system (such as Aeris 1, Aeris 2 or Certus), an Optis system, a multimodal system such as a combination intravascular imaging and pressure monitoring system, a hemodynamic display having a pressure data input. Embodiments of the disclosure can be integrated with the specialized processors and computing devices used in a pressure sensing, OCT, or IVUS system to measure the applicable data and generate the outputs and intermediate steps to determine one or more diagnostic metrics and display them as discrete fixed values or as time varying values. In one embodiment, the intravascular data analysis or data collection system is selected from the group consisting of an intravascular pressure sensing system, an optical coherence tomography system and an intravascular ultrasound system. In one embodiment, the processor is selected from the group consisting of a pressure sensing system processor, a OCT system processor, a multimodal intravascular system processor, and an IVUS system processor.

BRIEF DESCRIPTION OF DRAWINGS

The figures are not necessarily to scale, emphasis instead generally being placed upon illustrative principles. The figures are to be considered illustrative in all aspects and are not intended to limit the disclosure, the scope of which is defined only by the claims.

DETAILED DESCRIPTION

Various data collection and analysis systems are available to obtain information with regard to the coronary system. The data obtained using a device from a blood vessel or derived data from intravascular or extravascular measurements associated therewith can be analyzed or displayed to provide correlations and extrapolations to assist researchers and clinicians. For example, various measurement systems and intravascular probes are available to determine fractional flow reserve (FFR) with respect to a blood vessel using a pressure-sensor based device. Intravascular ultrasound (IVUS) can also be used in probes to image portions of a blood vessel. In turn, optical coherence tomography (OCT) is an imaging modality that uses an interferometer to obtain distance measurements relative to a blood vessel or objects disposed therein.

Intravascular data collection devices can be used to generate and receive signals that include diagnostic information relative to the blood vessel in which they are used. These devices can include without limitation imaging devices, such as optical or ultrasound probes, pressure sensor devices, and other devices suitable for collecting data with regard to a blood vessel or other components of a cardiovascular system.

Figure 1:
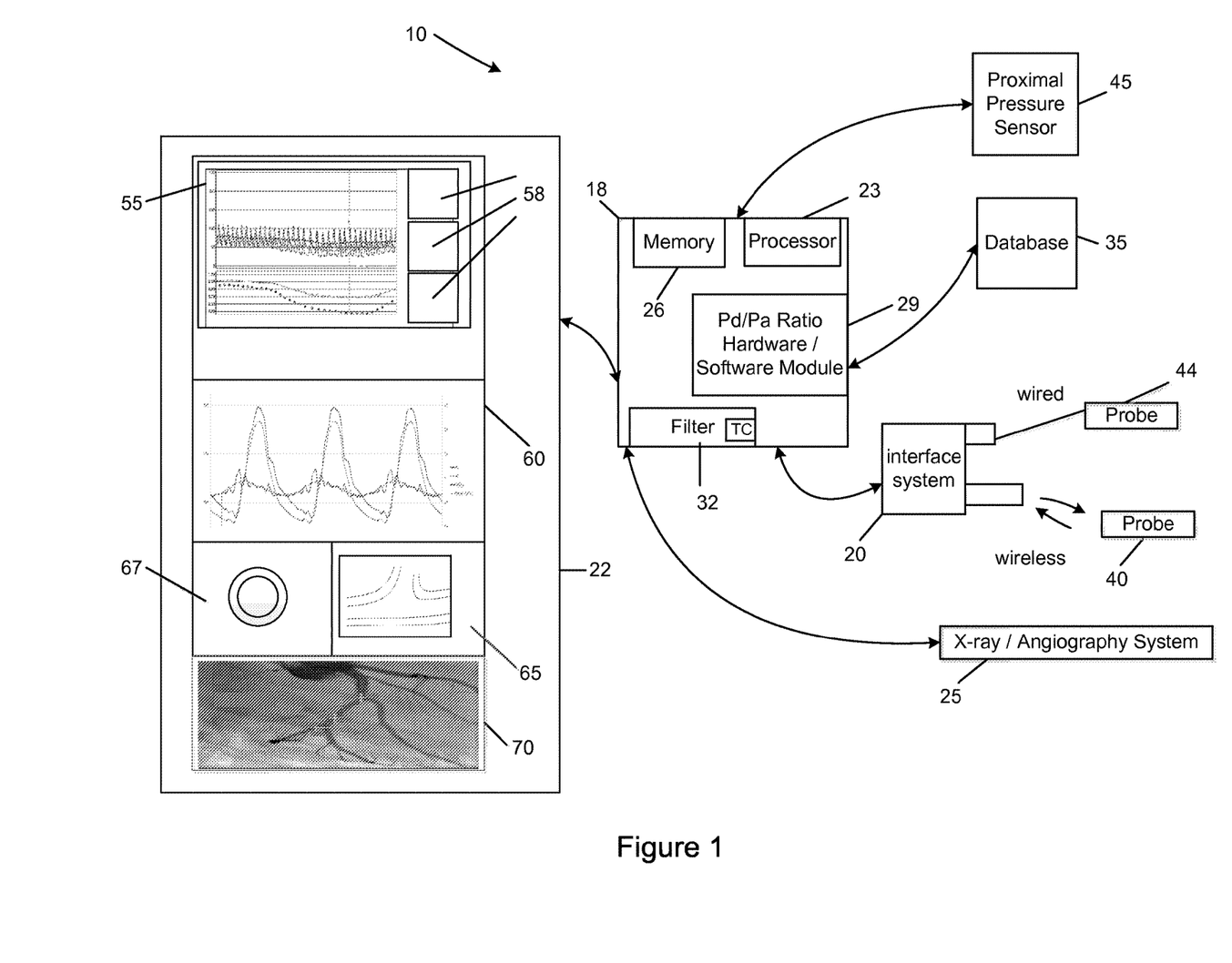
FIG. 1 is a schematic diagram of an intravascular data collection and display system that includes a minimum or threshold-based plot of pressure value ratios in accordance with an illustrative embodiment of the disclosure.

In part, the disclosure relates to intravascular data collections systems and related methods by which intravascular data collected by an intravascular probe can be transformed or analyzed by a processor-based system. The results of such analysis and transformation can be displayed to an end user in various representations such as a display that is in communication with or part of a system such as a pressure monitoring system or intravascular data collection system. Examples of such systems are shown in FIG. 1. In part, using such data to generate one or more indices or ratios correlated with a physiological state of a patient is disclosed.

These ratios or indices are correlated with one or more cardiac system parameters or a patient state such as a stenosis, a treatment regimen, a stent, stent malposition, stenosis severity, stenosis location, infarct size, infarct severity, guiding treatment strategy, evaluating treatment effect, and diagnostic information to assess the need for additional therapy post procedure. The ratios described herein can be determined using pressure values obtained during a resting state of the subject in one embodiment. In another embodiment, the ratios described herein can be determined after the introduction of a hyperemic agent such as adenosine. The use of a hyperemic agent can amplify the associated waveforms in one embodiment.

In one embodiment, a Pd/Pa ratio is continuously calculated using samples of Pd pressure values obtained from one or more pressure sensors or other sampled data used to calculate a pressure value. In one embodiment, pressure data is collected using an intravascular data collection probe disposed in a subject's artery. Exemplary intravascular data collection probes include catheter-based or catheter delivered probes, guidewire based probes, imaging probes, ablation probes, ultrasound probes, interferometry-based probes, and other suitable data collection probes and devices. The Pa values are also obtained on a continuous basis from the guide or delivery catheter. The guide or delivery catheter is used to position and advance the intravascular probe through a region of interest in an artery such as a stenosis. The ratio can be calculated on a per sample basis and a one or more Pd/Pa ratios can be determined during each heart cycle. As a result, for a given cardiac cycle a plurality or set of Pd/Pa ratios are obtained.

In the set of Pd/Pa ratios, a minimum Pd/Pa ratio value can be identified. This minimum ratio corresponds to a particular heart cycle and can be identified as a minimum cycle pressure ratio index or as a minimum cycle ratio (MCR). Each MCR for a set of cardiac cycles can be displayed as numerical values or plotted on a display system as described herein. In one embodiment, each MCR is based upon a cardiac cycle rather than a subset or portion thereof. In one embodiment, the MCR is a diagnostic metric that is generated using sampled intravascular data such as a pressure data. In one embodiment, the sampled data is obtained during diastole and systole.

As an example, if a sample rate of 100 Hz is used to collect Pd and Pa data, for an exemplary one second cardiac cycle, the cycle includes about 100 sample points. These 100 points can be used to determine 100 Pd/Pa ratios. From that set of 100 ratios, a minimum ratio can be identified as the MCR for that cardiac cycle. This process can be repeated for multiple cardiac cycles and plotted over time as shown for example in FIG. 4A. In one embodiment, the sample rate ranges from about 10 Hz to about 100 Hz. In one embodiment, the sample rate ranges from greater than about 25 Hz. In one embodiment, the sample rate ranges from about 100 Hz to about 2000 Hz. In addition, a cardiac cycle can be analyzed using flow curves, EKG, pressure waveforms, and other metrics in conjunction with using MCR values to diagnose one or more states of interest for a subject.

In one embodiment, the methods of determining a ratio as disclosed herein may not be or are not dependent upon ECG triggering or landmark identification. In one embodiment, methods of determining a ratio as disclosed herein may detect a heart rate as an input to adjust a filter parameter such as a sampling period, the time constant or other filter parameter. In one embodiment, ECG triggering or landmark identification is used to determine a heart rate or other input put parameter of the systems and methods. In another embodiment, the maximum pressure reduction in a heart cycle is also identifiable using the methods and systems disclosed herein independent of where such a maximum pressure reduction occurs in a given cardiac cycle. Thus, instead of being determined solely with regard to diastole, the minimum cycle ratio and related methods of the disclosure can identify where and when a maximum pressure reduction occurs in a given cardiac cycle. This identification can be performed whether such a pressure reduction occurs in diastole or systole.

Figure 5A:
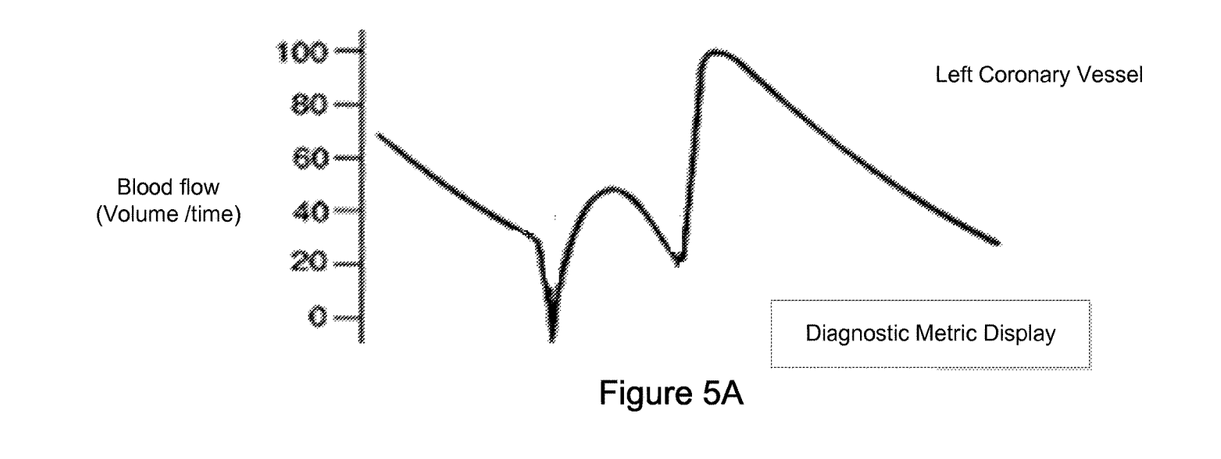
FIGS. 5A and 5B are exemplary plots depicting blood flow patterns in the left and right coronary system and include a diagnostic information display panel or interface in accordance with an illustrative embodiment of the disclosure.
Figure 5B:
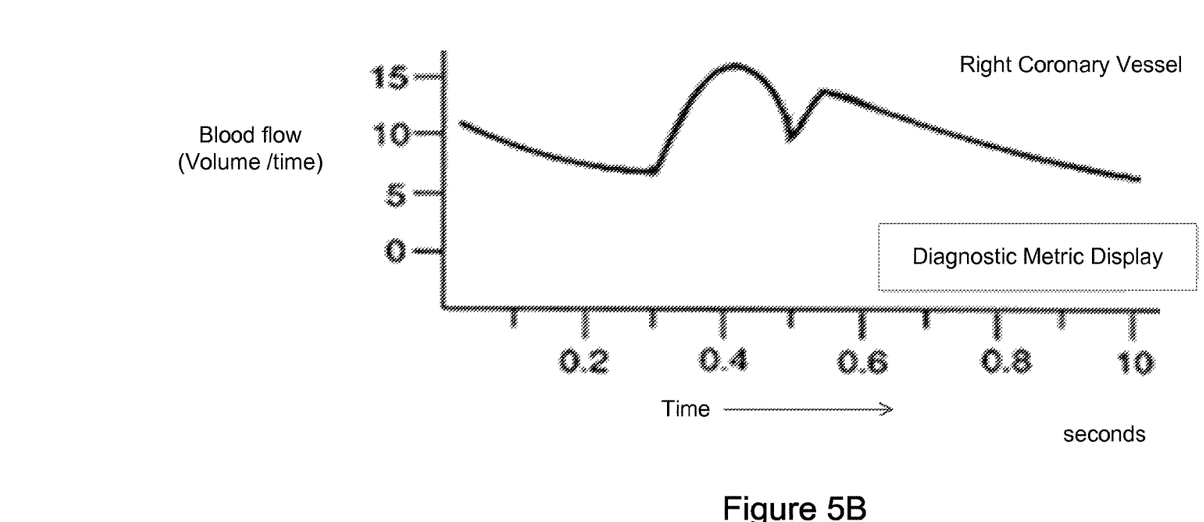

Accordingly, embodiments of the disclosure offer greater flexibility and improved accuracy relative to other approaches because the methods and associated ratios are independent or otherwise insensitive to whether the pressure values used to determine a ratio are measured in the left or right coronary system. Some exemplary graphs of flow details relating to the right and left coronary system are shown in FIG. 5. Compared to indexes using pressure averaging over several heart cycles, the minimum cycle ratio may also be more sensitive to changes that occur when the sensor is pulled back across lesions. Thus, after vessel revascularization has occurred or during a pressure pullback the minimum cycle ratio may be more sensitive to pressure changes when compared to a full cycle Pd/Pa. This sensitivity, which can manifest as smaller pressure drops being displayed as higher amplitude values on a display system, can be useful when tracking MCR values during a pullback to locate a stenosis, evaluate the impact after stenting, assess a side branch, and diffuse disease or other blood vessel features. The greater sensitivity makes the pressure change easier to detect when, for example, a stenosis is identified based on a change in MCR.

In one embodiment, to improve the consistency of a given minimum cycle ratio MCR value, the ratio can optionally be averaged over a number of heart cycles. In one preferred embodiment, the MCR is not averaged over multiple cardiac cycles, but instead is determined on a per cycle basis. The MCR can be displayed as a number on a screen, as a curve, a plot of discrete points, and combinations of the foregoing or in other representations that are based upon, correlated with, or derived from the MCR.

In one embodiment, a display system provides a user interface that includes features that allow certain conditions or other parameters to be used when determining a MCR or other ratio. After recording values or activation, the system can be configured to display the lowest ratio in the entire recording or after a pre-selected number of heart cycles based on user selections via a user interface. Each MCR values provides a metric to identify on a per heart cycle basis the occurrence of a maximum pressure reduction in a heart cycle, regardless of pressure sensing location and without ECG triggering or landmark identification. An exemplary system and components thereof of for determining MCR values is described with regard to FIG. 1.

FIG. 1 depicts a cath lab system 10 suitable for analyzing cardiac systems. The system 10 can include various systems such as a data collection and analysis system 18, an interface system 20, a display system 22 and an x-ray system 25 such as an angiography system 25. Some non-limiting examples of intravascular data collection and analysis systems 18 or a component thereof can include a RadiAnalyzer, a RadiAnalyzer Xpress, a Quantien, an Aeris system, an Optis system, a multimodal system such as a combination intravascular imaging and pressure monitoring system, a hemodynamic display having a pressure data input.

The data collection and analysis system 18 can include a processor 23 such as a microprocessor, a memory 26, a filter 32 having an associated time constant TC, and one or more software modules, circuits, or hardware components such as a diagnostic metric generator 29 such as for example a Pd/Pa ratio hardware component or software module 29. The processor can be in electrical communication with a circuit board of a pressure sensing, OCT, IVUS, or other intravascular data collection system. The time constant TC can be updated with or adapted based on a measured parameter or preset value or be user selected. The data collection and analysis system 18 can also review historic data stored in a database 35 from prior intravascular and extravascular data collection sessions. The results of determining one or more ratios, curves, or other values as described herein can also be stored in database 35. One or more databases can be used for various data sets as applicable.

In part, embodiments of the disclosure relate to various features of pressure sensing devices, measurement systems, and software relating thereto suitable for determining ratios based upon signals sampled from an intravascular data collection probe such as probes 40 or 44. A guidewire-based probe 40, 44 with a semiconductor device that includes components that undergo electrical changes in response to pressure changes can be used to perform pressure monitoring. The embodiments described herein support methods of performing the methods, ratio determination and measurements using a guidewire-based probe and associated software and electrical components of a data collection and analysis system 18. A wired probe 44 or a wireless probe 40 can be used to transmit data that is received by an interface system 20, system 18, or system 22. A sensor 45 such as the proximal pressure sensor of a guide or delivery catheter can also receive proximal pressure values (Pa) such as aortic pressure values.

System 18 can perform measurement calculations based on signals sampled from the intravascular probe. Alternatively, system 18 can receive signals encoding results of calculations performed using circuitry or processing elements disposed in the probe such as for example in the probe's proximal connector. System 18 can also include software, control systems, and data analysis and display devices and processors suitable for graphing and displaying pressure values, FFR values, MCR values, sampled Pa values, sampled Pd values, moving averages and other values relating to the foregoing.

The interface system 20 is connected to one or more circuits or signal processing or control elements. These circuits, elements, and other components of a given intravascular measurement system are used to convert the time varying electrical signals from the guidewire-based probe by sampling a probe 40, 44 or sensor to generate Pd and Pa values which can be received by one or more systems of FIG. 1. The time varying electrical signals can be currents, voltages, resistance changes, or other data correlated with MCR values. The interfaces and displays are formatted and programmed to display these values and others ratios and parameters as described herein using the display system 22.

The display system 22 can include panels, user interfaces, and other screens suitable for displaying pressure data, such as Pd and Pa values, or data derived therefrom 55, 58, angiography images 70, IVUS or OCT images 67, 65, and other intravascular images and data. The displays 22 or interfaces 20 can be part of or in electrical communication, such as by wireless communication, with system 18 that receives data from a guidewire-based probe, OCT, FFR, IVUS, or other systems.

The angiography system 25 can be used to generate cine sequences by which a pressure wire can be observed before and after a data collection pullback. In one embodiment, the display system simultaneously displays a cine sequence while displaying MCR values that change in time as a pressure sensor is pullback through a vessel. The changes in the MCR values can be used to determine areas of stenosis along the pullback path in the artery. These stenosis locations can be identified using a cursor or electronic annotation tool to mark candidate regions for stenting on one or more angiography frames of the cine sequence or for further imaging using IVUS, OCT or another imaging or data collection modality.

Figure 2A:
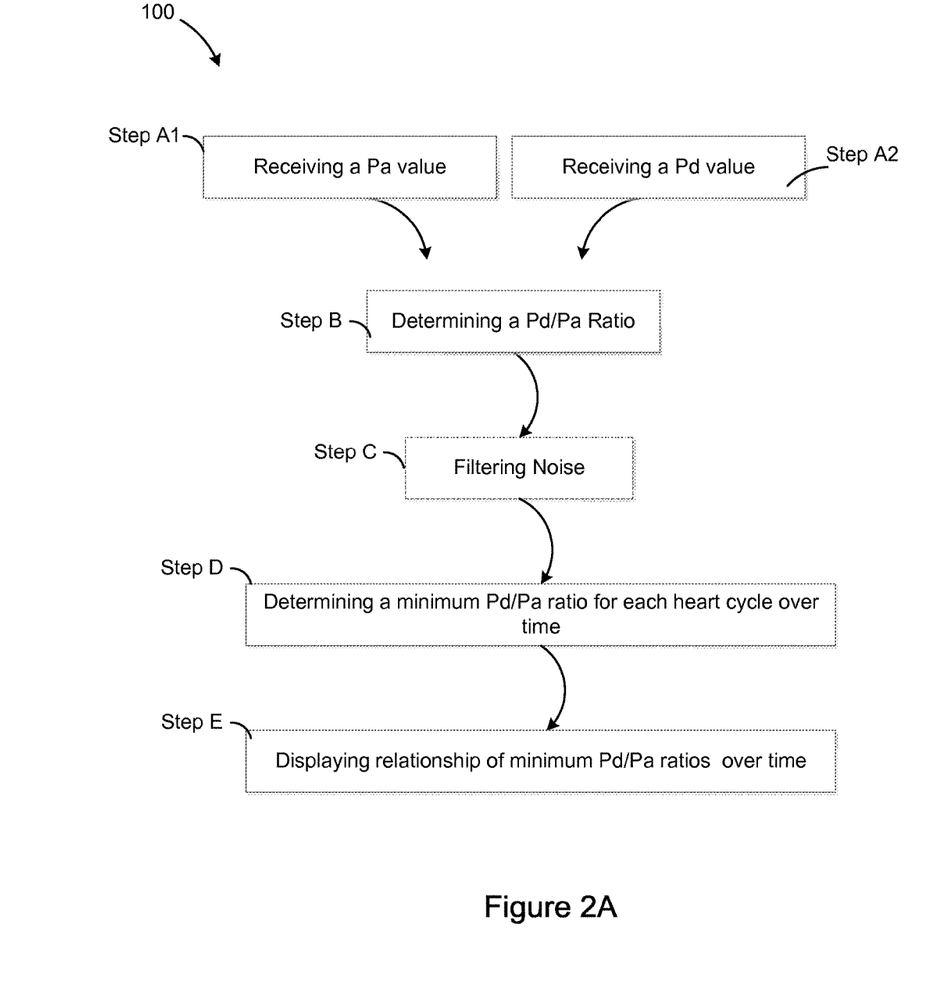
FIG. 2A is a flow chart of an exemplary method of intravascular data analysis and display in accordance with an illustrative embodiment of the disclosure.
Figure 2B:
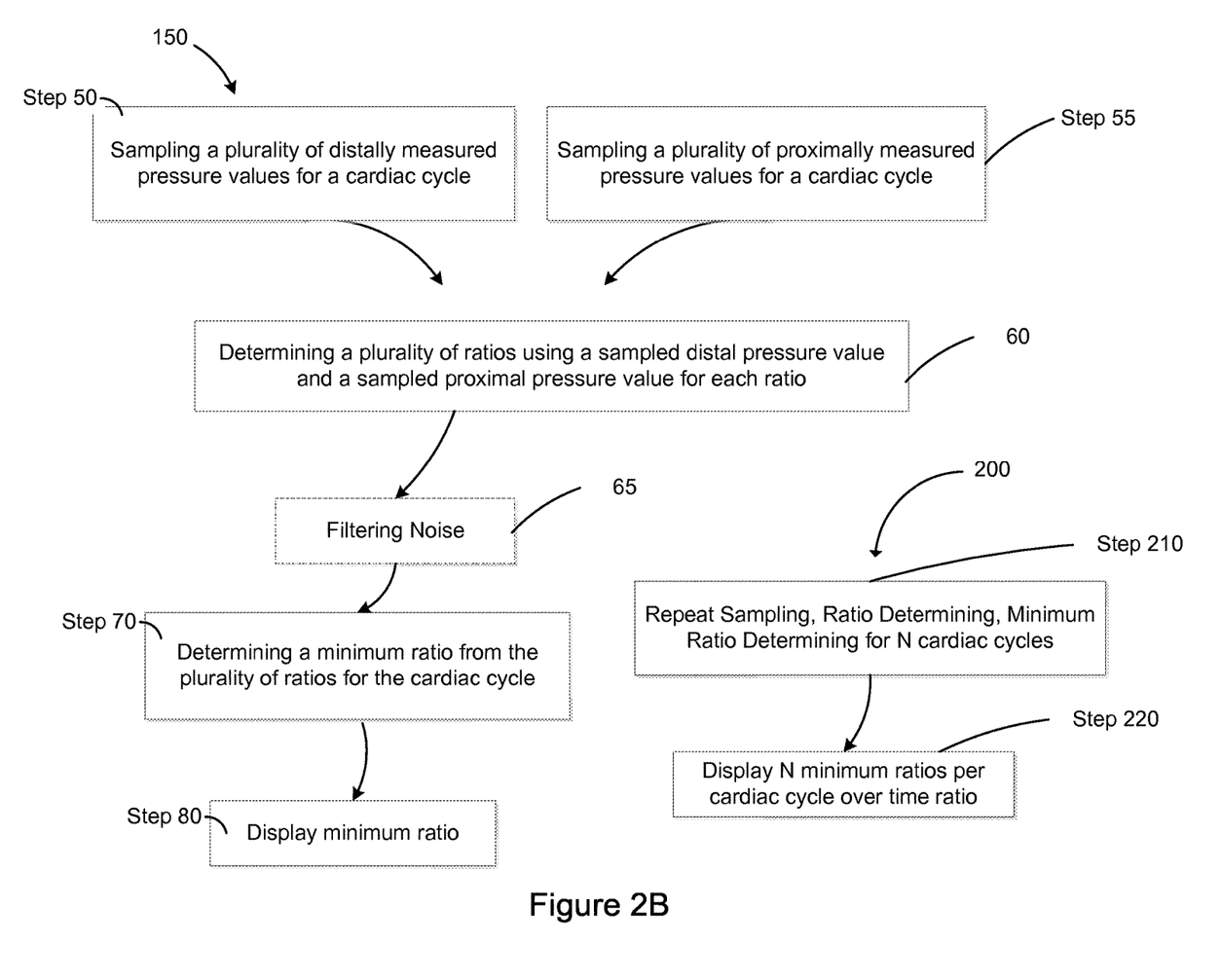
FIG. 2B is a flow chart of an exemplary method of intravascular data analysis and display in accordance with an illustrative embodiment of the disclosure.

The Pa pressure values obtained from a pressure sensor such as mounted on a catheter or guidewire, or otherwise calculated using other measurements, can be used in conjunction with Pd pressure values sampled from a given intravascular probe to determine one or more ratios such as MCR values. These ratios can be displayed or plotted as described herein. FIGS. 2A and 2B show exemplary methods 100 and 150 respectively for determining one or more such ratios. Although the ratio are described here as minimum values, the values can also be determined as falling within a particular threshold or other range such as being within a certain percentage of an absolute minimum value or a stand deviation from a minimum value.

Although a minimum value is preferred in certain circumstances, in circumstances where a minimum value is referenced herein a threshold value can also be used that is not a minimum but within range of a minimum value by a predetermined threshold. Thus, a threshold value of between greater than about 0% to less than about 20% of a minimum value such as a Pd/Pa ratio can be used on a per cycle basis in one embodiment. In one embodiment, the Pd/Pa ratio is a diagnostic metric that can be displayed relative to a user interface or display panel of an OCT, IVUS, pressure sensing, flow sensing or other system. The diagnostic metric facilitates decision making relative to a subject for a user such as a clinician.

As shown in FIG. 2A, the method includes the steps of receiving a Pa value and receiving a Pd value. These steps A1 and A2 can be performed separately or together. The values can be received by a component of system 10 such as data collection and analysis system 18. In one embodiment, multiple Pd and Pa values are received over time and are associated with individual cardiac cycles during which they are collected. The method also includes determining a Pd/Pa ratio (Step B) based upon the received Pa and Pd values. In one embodiment, multiple Pd/Pa ratios are determined. An optional filtering step (Step C) may be part of the method. Filtering the Pd/Pa ratio traces or curves can be used to smooth such traces or curves by removing noise. The filter can be of various types such as a low pass filter, a high pass filter, a moving average filter, similar filters or combinations thereof, and other suitable filters. The time constant TC for the filter can range from about 10 ms to about 500 ms.

The application of a filter to the ratio curve increases the repeatability of the MCR value for a given cardiac cycle in one embodiment. In one embodiment, the time constant TC will affect the MCR value. This is important for instance when a patient has greatly fluctuating heart rate, bradycardia or tachycardia. The TC constant can be a pre-selected constant in one embodiment having a TC range from about 10 ms to about 500 ms, preferred subset between 100 and 300 ms. In one embodiment, the TC is adaptive and can change over time or have a relationship with one or more parameters such as heart cycle length or another cardiac system or vessel parameter. For example, an adaptive TC can be used that is determined as a percentage of the heart cycle length. The heart cycle length can be measured during a data collection session and used as an input to generate the adaptive TC. An adaptive TC can be of the form of TC=a (heart cycle length), wherein a is a percentage. The percentage for such an adaptive TC can range from about 1% to about 50% of a heart cycle length. The TC can be adjusted by a user via a user interface, be a fixed valued stored in the data collection system, be updateable via network or firmware updates, or otherwise configured as is suitable for a given scenario. The user interface can be displayed on system 10 via display 22.

Still referring to FIG. 2A, given that one or more Pd/Pa ratios have been determined, the method also includes the step of determining a minimum Pd/Pa ratio (MCR) (Step D). A minimum, a relative extrema, or a value correlated or derived from the foregoing can be used as a diagnostic metric in one embodiment. A threshold value such as a percentage of a minimum ratio can also be used for this and other MCR determination embodiments. This determination process can be performed for each heart cycle over time. Once one or more MCR values have been determined these ratios can be displayed as numerical values on a display system or plotted over time such as shown in the figures of the disclosure (Step E). FIG. 2B shows another exemplary embodiment of method 160 of determining and displaying a MCR. Steps 50 and 55 can be performed together or separately. Step 65 is an optional filtering step. Steps 60, 70, and 80 can be performed as shown. The process of FIG. 2B further illustrates that multiple MCRs can be displayed for N cardiac cycles over time as discrete points, values or curves on a display as shown in process flow 200. In the method 200, steps 210 and 220 are performed. Filtering of noise can also be performed as part of method 200. Thus, the steps include sampling a plurality of distally measured pressure values for a cardiac cycle. Sampling a plurality of proximally measured pressure values for a cardiac cycle is another step. Determining a plurality of ratios using a sampled distal pressure value and a sampled proximal pressure value for each ratio is a step. Optionally, noise filter can be performed. Determining a minimum ratio from the plurality of ratios for the cardiac cycle can be performed. The ratio can then be displayed as a value, a value that changes, or as a plot of values or points. Repeating Sampling, Ratio Determining, Minimum Ratio Determining for N cardiac cycles can be performed iteratively for N cycles wherein is 1 or greater than 1. In one embodiment, the method includes displaying N minimum ratios per cardiac cycle over time ratio.

Figure 3A:
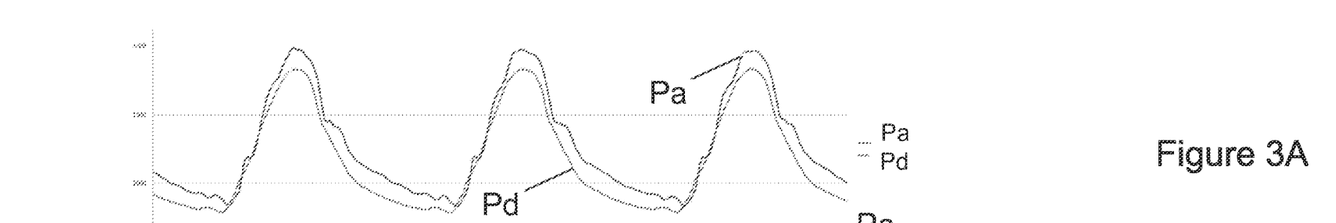
FIGS. 3A-3F are a series of intravascular data sets or plots in accordance with an illustrative embodiment of the disclosure.
Figure 3B:
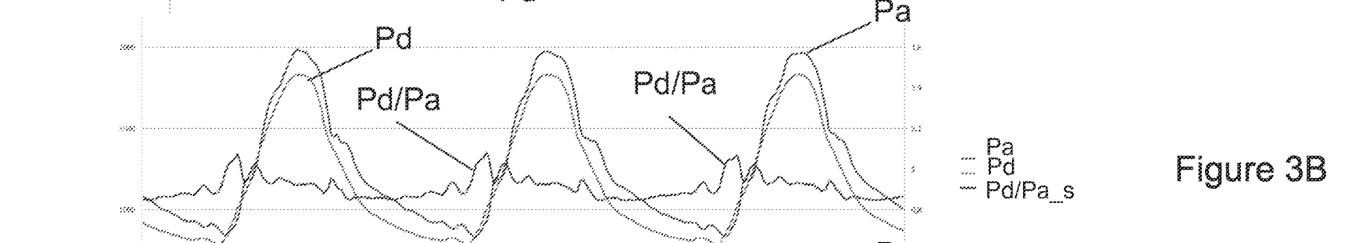
Figure 3C:
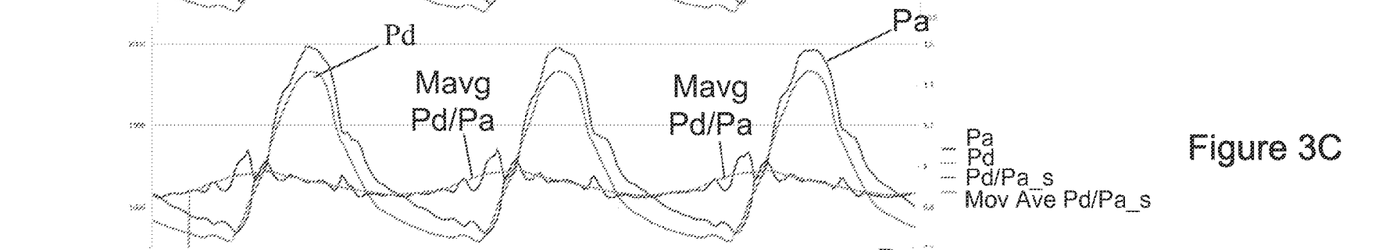
Figure 3D:
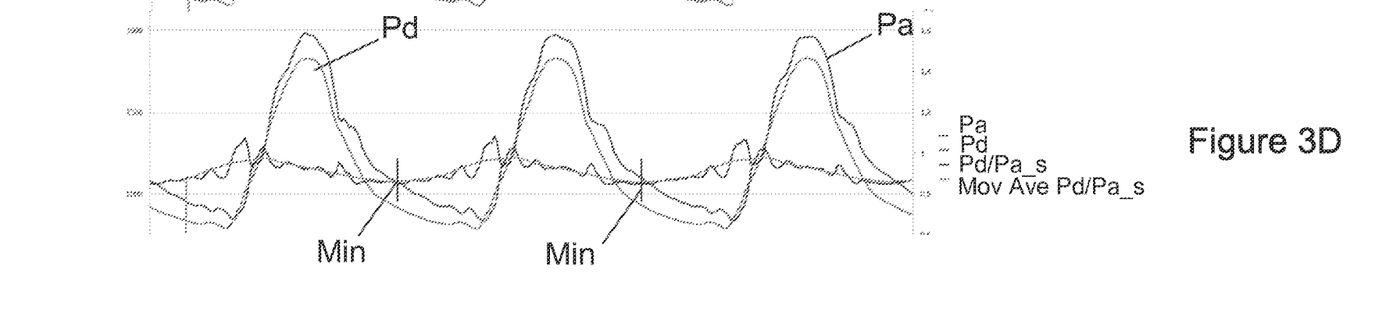
Figure 3F:
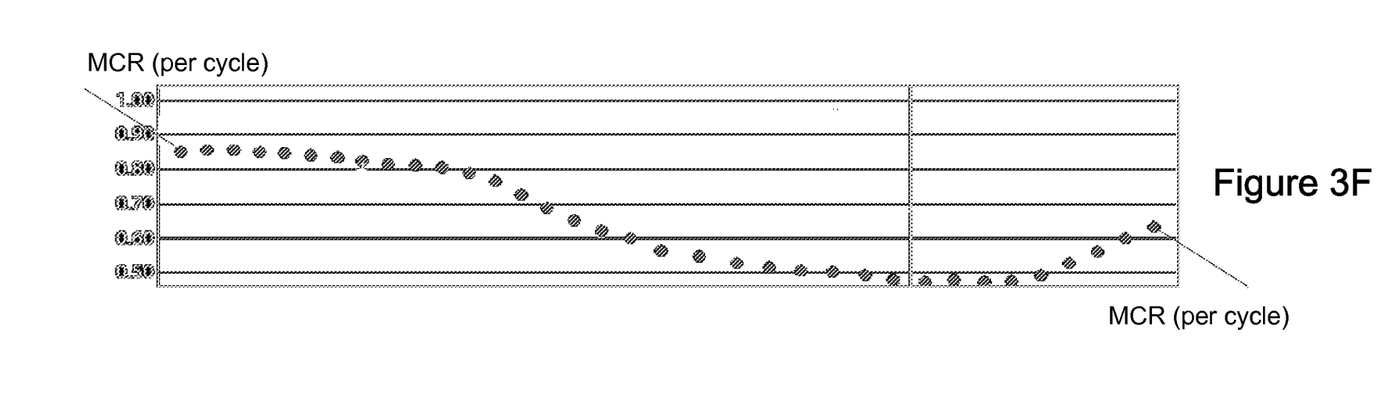
Figure 4A:
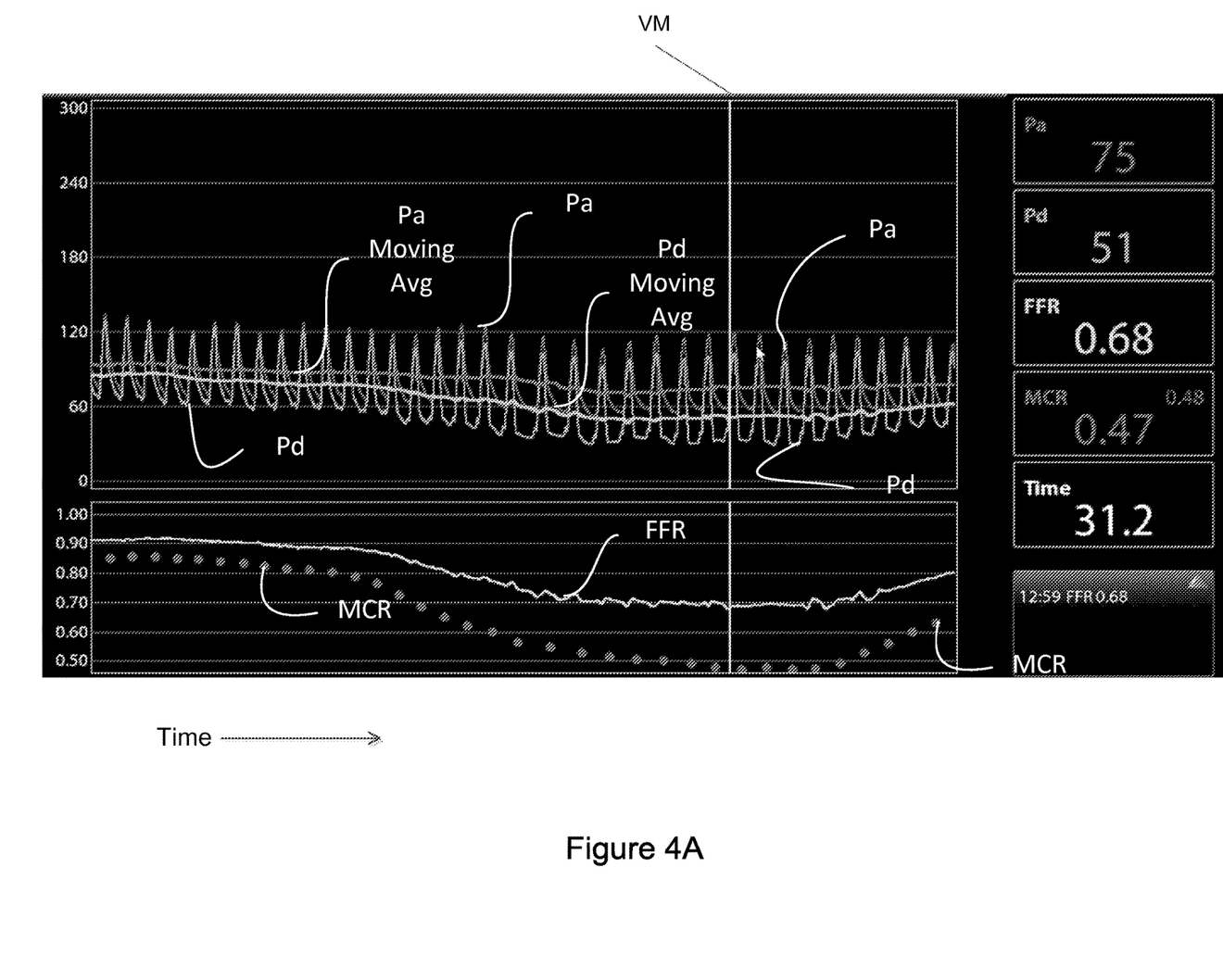
FIGS. 4A and 4B are data displays of intravascular data-based information and relationships over time and on a per heart cycle basis and described herein in accordance with an illustrative embodiment of the disclosure.
Figure 4B:
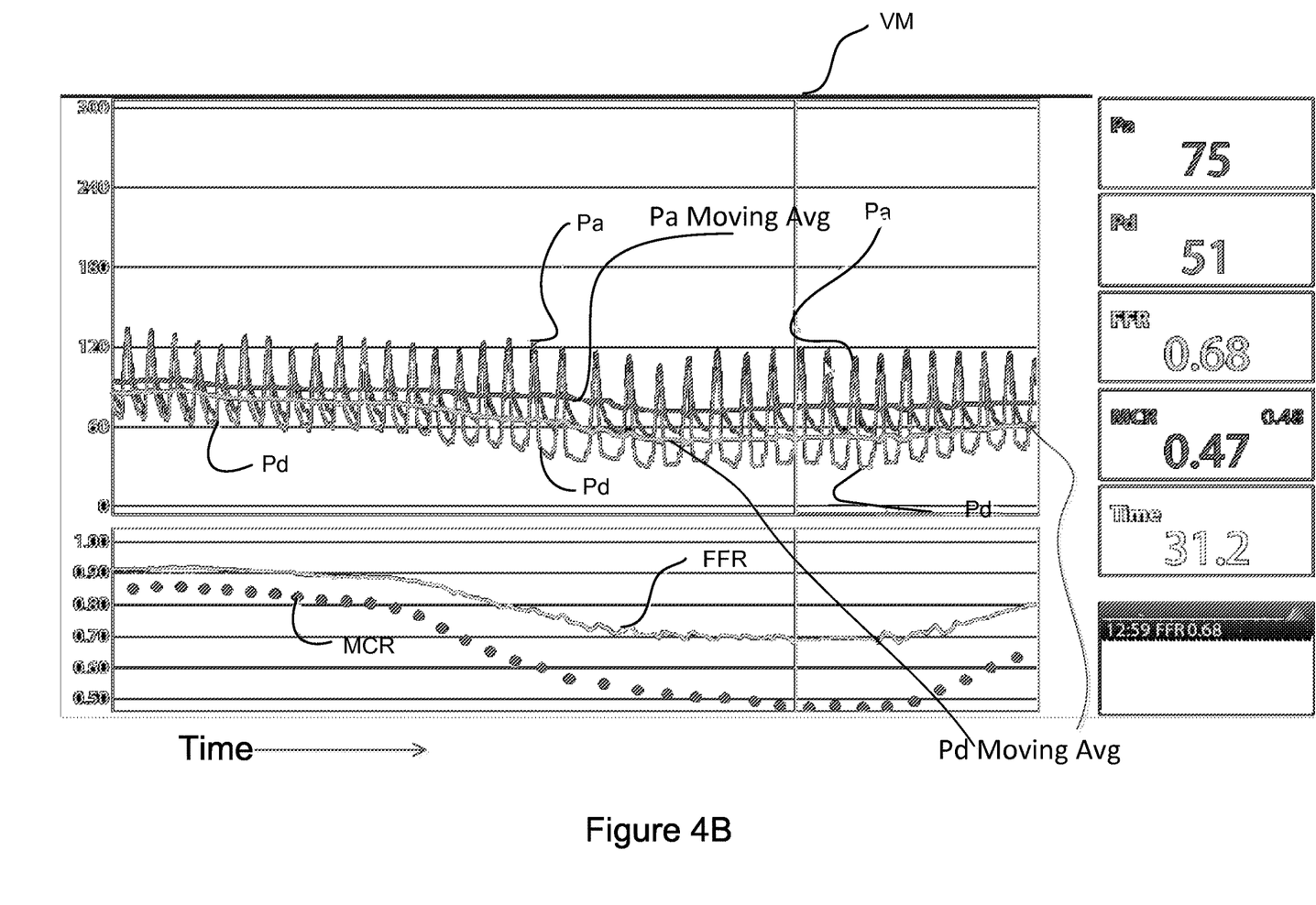

FIG. 3A shows a plot of sampled Pa and Pd values for multiple cardiac cycles. The Pa curve is generally above the Pd curve. FIG. 3B shows the plot of FIG. 3A with the addition of a curve corresponding to the Pd/Pa ratios. In FIG. 3C, the plot of FIG. 3B is shown with the addition of a moving average of the Pd/Pa ratios. In FIG. 3C, the Pd/Pa curve has been smoothed by applying a filter having a time constant TC prior to determining the moving average. The application of such a filter is optional, but can be advantageous under certain scenarios in order to increase repeatability of the MCR measurement regardless of signal noise or fluctuating heart rate. In FIG. 3D, the plot of FIG. 3C is shown with the addition of vertical markers corresponding to the minimum Pd/Pa ratios for two cardiac cycles. These minimum values can be plotted as MCR values over time such as shown in FIG. 3F or 4A and 4B. The images shown in FIG. 3A-3D illustrate the method of generating data using an MCR determination method such as disclosed with respect to FIGS. 2A and 2B. These figures or portions thereof can also be displayed to a user or derivatives thereof to facilitate diagnosis of a subject.

Figure 3E:
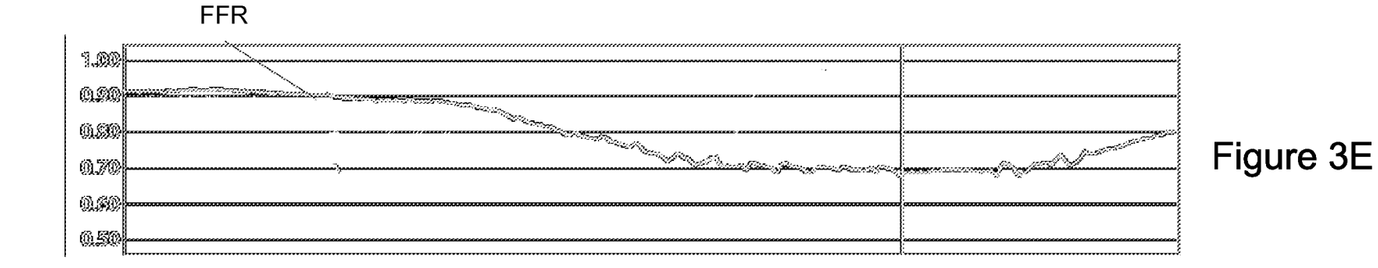

FIG. 3E shows a plot of FFR values. The FFR values range from about 0.6 to below about 1. The FFR values are plotted versus time with the FFR value be calculated on a per sample basis. The FFR values are determined using the Pd/Pa ratios during hyperemia and averaged over one or several heart cycles over the heart cycles recorded. Measurement of fractional flow reserve (FFR) with a pressure wire is used to as provide guidance for coronary stenting decisions. A distal FFR reading ≥0.8 measured in a coronary branch indicates that Percutaneous Coronary Intervention (PCI) can be safely deferred, because lesions in the branch are not sufficiently narrowed to induce ischemia under hyperemic conditions. Conversely, a distal FFR value <0.8 indicates the need for treatment, usually by implantation of a stent. Transitions in MCR values can be used in parallel with or in lieu of FFR values to facilitate stent planning.

FIG. 3F shows a plot of discrete MCR values over time. The MCR values are discrete because they are determined on a per heart cycle basis in the embodiment shown. The MCR values are determined as the minimum Pd/Pa ratio for the sampled Pd and Pa values for a given heart cycle.

FIG. 4A and an alternative graphical representation thereof, FIG. 4B, also show the FFR values of FIG. 3E and the MCR values of FIG. 3F in the bottom panel of the screen. The sampled Pd and Pa values are shown as a tracing in the top panel. In addition, the moving average of the Pa values (Pa Moving Avg) and the Pd values (Pd Moving Avg) are also shown. The Pa Moving Avg is the curve passing through the Pa and Pd peaks. The Pd Moving Avg is the curve disposed below the Pa Moving Avg. In the region of the screen to the right, from top to bottom Pa, Pd, FFR, MCR, and time values are shown corresponding to the position of the vertical marker VM. The vertical marker VM can be programmed to be displayed at a predetermined value or adjustable to cycle through a set of preset positions. The vertical marker VM can also be arbitrarily positioned by the user. As shown, the VM is close to the Pd/Pa minima and MCR minima. In one embodiment, multiple panels of data or user interface information such as shown in FIGS. 4A and 4B are displayed with a plot or a fixed value or a time varying value of MCR, Pa, Pd, FFR, Time, Pa moving, Pd moving, and averages and weighted combinations of the foregoing. In one embodiment, a display panel with MCR values varying over time is plotted relative to time varying FFR values to facilitate stent planning or other characterization or diagnosis of an artery.

These figures and user interfaces screens can be used with intravascular and angiography images to make stent decisions, identify regions of interest from a diagnostic standpoint, and inform other cardiac system treatment decisions as diagnostic tools. These ratios are also advantageous relative to other approaches for the various implementation and reliability details described herein.

FIGS. 4A and 4B show MCR both at rest and during hyperemia (with the MCR values determined at the same time as FFR). The MCRs determined with the subject at rest may be used to predict the FFR value at hyperemia. Further, MCRs during hyperemia may be used to amplify the stenosis induced pressure difference during hyperemia, as compared to FFR. In one embodiment, a user of the systems, methods, and displays disclosed herein can review a given display of MCR values over time, before a procedure, during a procedure, or after a procedure to diagnoses stenosis severity, stenosis location, guiding treatment strategy, evaluating treatment effect, assessing the need for additional therapy post procedure.

FIGS. 5A and 5B are exemplary plots depicting blood flow patterns in the left and right coronary system. In FIG. 5A, the left coronary vessel's blood flow in terms of blood volume per unit time versus time is shown. In FIG. 5B, the right coronary vessel's blood flow in terms of blood volume per unit time versus time is shown. The ratios and indexes disclosed herein are suitable for describing one or more cardiac cycles and are suitable for use with pressure data collected from either the left or right coronary vessels even though the flow properties of the two vessels differ over time. In one embodiment, the plots of FIGS. 5A and 5B can be displayed as part of a display or user interface of an OCT, IVUS, pressure measurement, flow measurement, or other cardiovascular diagnostic/data collection system as described herein.

In one embodiment, the diagnostic metrics described herein are not specific to a phase of the cardiac cycle such as diastole. The "instantaneous wave free ratio", or iFR, is a method that attempts to correlate an iFR to the more widely used Fractional Flow Reserve, or FFR. In contrast with an embodiment of the disclosure, as part of the process of calculating the instantaneous wave free period, the aortic pressure and coronary artery pressure are averaged during a period of diastole. This iFR methodology is based upon the assumption that the vascular resistance is minimized during diastole and thus would allow lesion assessment in a resting condition without the use of hyperemic agents.

There are challenges and uncertainties associated with using an instantaneous wave free ratio. Calculation of a ratio in a specific window in diastole requires precise gating of signals such as by searching for specific values in the pressure waveform. The signal processing and analysis of waveforms adds a degree of complexity in order to use such a ratio and the reliance on diastole may skew the output. Further, as noted above, using the ratio calculated during diastole is based on the assumption that maximum blood flow occurs in diastole. This is not necessarily the case in the right coronary system where flow may be higher in systole, using a diastolic index in the right coronary vasculature may therefore potentially lead to an erroneous assessment of lesion severity. Diastole is a subset of a cardiac cycle. As a result, relying on data collected during a fixed subset of the cardiac cycle may be a source of unreliable results under various circumstances. In one embodiment, the diagnostic methods and associated output metrics described herein are not obtained using such a fixed subset of the cardiac cycle. In one embodiment, a method of the disclosure generates a diagnostic metric based on one or more cardiac cycles or a subset of the cardiac cycle that includes diastole and systole.

Non-Limiting Software Features and Embodiments for Determining Diagnostic Metrics Such as Ratios and Indices Based on Intravascular Probe Data The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic device, network PCs, minicomputers, mainframe computers, and the like. The disclosure can also be practiced in distributed computing environments where tasks are performed by remote processing devices that are linked through a communications network such as in different rooms of a catheter or cath lab.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "correlating" or "detecting" or "measuring" or "calculating" or "comparing" "generating" or "sensing" or "determining" or "displaying," or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The present disclosure, in some embodiments, also relates to apparatus for performing the operations herein. This apparatus may be specially constructed for the required purposes, or it may comprise a general purpose computer selectively activated or reconfigured by a computer program stored in the computer. Various circuits and components thereof can be used to perform some of the data collection and transformation and processing described herein.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present disclosure is not described with reference to any particular programming language, and various embodiments may thus be implemented using a variety of programming languages.

Embodiments of the disclosure may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other programmable logic device), discrete components, integrated circuitry (e.g., an Application Specific Integrated Circuit (ASIC)), or any other means including any combination thereof. In a typical embodiment of the present disclosure, some or all of the processing of the data collected using an OCT probe and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating a fixed or time varying diagnostic metric, fixed or time varying ratios based upon sampled pressure values, sampling of intravascular data including sampling based on one or more cardiac cycles or a subset of the cardiac cycle that includes diastole and systole and otherwise display such ratios and options which change how they are determined for a given pressure data collection session, and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as resistance changes, voltage changes, current changes, guidewire-based probe data, intravascular pressure data, ratios, indices and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

It is to be understood that the figures and descriptions of the disclosure have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

What is claimed is:

1. A method of determining one or more diagnostic metrics to assess a blood vessel using intravascular data comprising:
   sampling a sensor of an intravascular data collection probe disposed in the blood vessel at a sampling rate during a pullback of the intravascular data collection probe through the blood vessel to obtain a plurality of sampled distal pressure (Pd) values;
   receiving, at an intravascular data processing system, the plurality of sampled distal pressure (Pd) values and a plurality of proximal pressure (Pa) values;
   determining, using the intravascular data processing system, a plurality of sets of Pd/Pa ratios based on the plurality of sampled distal pressure (Pd) values and the plurality of proximal pressure (Pa) values, wherein each of the plurality of sets of Pd/Pa ratios includes Pd/Pa ratios that are determined through an entirety of one heart cycle;
   determining, using the intravascular data processing system, a plurality of minimum Pd/Pa ratios, wherein each of the minimum Pd/Pa ratios is a minimum within one of the sets of Pd/Pa ratios over the entirety of the corresponding heart cycle; and
   controlling a display system to generate a plot of a moving average of the plurality of minimum Pd/Pa ratios over time during the pullback.

2. The method of claim 1, further comprising, before determining the plurality of minimum Pd/Pa ratios, filtering the plurality of sets of Pd/Pa ratios using a filter having a time constant, wherein the time constant is in a range of 1% to 50% of a heart cycle length.

3. The method of claim 1 further comprising:
   identifying a change in the plurality of minimum Pd/Pa ratios as an indication of a stenosis in the blood vessel.

4. The method of claim 1, further comprising displaying a user interface comprising the plot.

5. The method of claim 1, further comprising controlling the display system to display at least one of a FFR value, a Pd value, a Pa value, a Pa moving average, a Pd moving average, or an intravascular image.

6. The method of claim 1, wherein the method further comprises controlling the display system to display an indication of an overall minimum Pd/Pa ratio.

7. An intravascular data analysis system to assess a blood vessel comprising:
   an interface system configured to receive intravascular pressure data including a plurality of distal pressure (Pd) values measured by an intravascular data collection probe and a plurality of proximal pressure (Pa) values during a pullback of the intravascular data collection probe through the blood vessel;
   a display system;
   one or more memory storage devices comprising instructions; and
   a processor in communication with the interface system, the display system, and the one or more memory storage devices, wherein the processor is configured to execute the instructions to:
   determine a plurality of sets of Pd/Pa ratios based on the plurality of distal pressure (Pd) values and the plurality of proximal pressure (Pa) values, wherein each of the plurality of sets of Pd/Pa ratios includes Pd/Pa ratios that are determined through an entirety of one heart cycle,
   determine a plurality of minimum Pd/Pa ratios, wherein each of the minimum Pd/Pa ratios is a minimum within one of the sets of Pd/Pa ratios over the entirety of the corresponding heart cycle, and control the display system to generate a plot of a moving average of the plurality of minimum Pd/Pa ratios over time during the pullback.

8. The system of claim 7, wherein the processor is configured to, before determining the plurality of minimum Pd/Pa ratios, filter the plurality of sets of Pd/Pa ratios using a filter having a time constant, wherein the time constant is in a range of 1% to 50% of a heart cycle length.

9. The system of claim 7, wherein the processor is further configured to execute the instructions to control the display system to display an indication of an overall minimum Pd/Pa ratio.

10. The system of claim 7, wherein the plot comprises a discrete point for each of the plurality of minimum Pd/Pa ratios.

11. The system of claim 7, wherein the processor is further configured to execute the instructions to track changes in the plurality of minimum Pd/Pa ratios during the pullback to identify a location of a stenosis in the blood vessel.

12. The system of claim 7, wherein the processor is further configured to execute the instructions to display a user interface comprising the plot.

13. The system of claim 7, wherein the processor is further configured to execute the instructions to identify a change in the plurality of minimum Pd/Pa ratios as an indication of a stenosis in the blood vessel.

14. The system of claim 7, wherein the processor is further configured to execute the instructions to control the display system to display at least one of a FFR value, a Pd value, a Pa value, a Pa moving average, a Pd moving average, or an intravascular image.

* * * * *